US012599601B2

(12) United States Patent
Kim et al.

(10) Patent No.: US 12,599,601 B2
(45) Date of Patent: Apr. 14, 2026

(54) ANTIFUNGAL COMPOSITION CONTAINING CARBAZOLE COMPOUND AS ACTIVE INGREDIENT

(71) Applicant: KOREA UNIVERSITY RESEARCH AND BUSINESS FOUNDATION, Seoul (KR)

(72) Inventors: Joon Kim, Seoul (KR); Young Kwang Park, Incheon (KR)

(73) Assignee: Korea University Research and Business Foundation, Seoul (KR)

( * ) Notice: Subject to any disclaimer, the term of this patent is extended or adjusted under 35 U.S.C. 154(b) by 927 days.

(21) Appl. No.: 17/771,563

(22) PCT Filed: Oct. 16, 2020

(86) PCT No.: PCT/KR2020/014164

§ 371 (c)(1),
(2) Date: Apr. 25, 2022

(87) PCT Pub. No.: WO2021/080256

PCT Pub. Date: Apr. 29, 2021

(65) Prior Publication Data

US 2022/0378783 A1 Dec. 1, 2022

(30) Foreign Application Priority Data

Oct. 23, 2019 (KR) ........................ 10-2019-0132073

(51) Int. Cl.

*A61K 31/496* (2006.01)
*A61K 31/4045* (2006.01)
*A61K 31/454* (2006.01)
*A61P 31/10* (2006.01)

(52) U.S. Cl.

CPC ........ *A61K 31/496* (2013.01); *A61K 31/4045* (2013.01); *A61K 31/454* (2013.01); *A61P 31/10* (2018.01)

(58) Field of Classification Search

CPC ............................ A61K 31/496; A61K 31/403
See application file for complete search history.

(56) References Cited

U.S. PATENT DOCUMENTS

2003/0220340 A1* 11/2003 Roberts ................ C07D 209/82 549/48
2004/0157837 A1 8/2004 Serbedzija et al.

FOREIGN PATENT DOCUMENTS

CN 104974141 A 10/2015
CN 109496211 A 3/2019
JP 2003-512371 A 4/2003
KR 10-2093409 B1 3/2020
WO WO 01/29028 A1 4/2001
WO WO 2008/147864 A2 12/2008
WO WO 2019/043064 A1 3/2019

OTHER PUBLICATIONS

Kwolek-Mirek & Zadrag-Tecza, FEMS Yeast Res., 2014, 14, 1068-1079 (Year: 2014).*

Park, Young-Kwang, et al. "Development of Carbazole Derivatives Compounds against *Candida albicans*: Candidates to Prevent Hyphal Formation via the Ras1-MAPK Pathway." Journal of Fungi 7.9, 2021, (16 pages).

Extended European search report issued on Oct. 11, 2023, in counterpart European Patent Application No. 20878783.8 (10 pages).

Lee, Hee-Yoon, et al. "Structure-activity relationship studies of the chromosome segregation inhibitor, Incentrom A." *Bioorganic & Medicinal Chemistry Letters* 18.16 (Jul. 9, 2008): pp. 4670-4674.

Zhu, Shi-Ping, et al. "Design, synthesis and antifungal activity of carbazole derivatives." *Chinese Chemical Letters* 25.2 (Nov. 21, 2013): pp. 229-233.

Berkow, Elizabeth L., and Shawn R. Lockhart. "Fluconazole resistance in *Candida* species: a current perspective." *Infection and drug resistance* 10 (Jul. 31, 2017): pp. 237-245.

Korean Office Action issued on Dec. 18, 2019 in corresponding Korean Patent Application No. 10-2019-0132073 (4 pages in Korean).

Korean Decision to Grant on Feb. 26, 2020 in corresponding Korean Patent Application No. 10-2019-0132073 (2 pages in Korean).

Chinese search report issued on Apr. 10, 2023, in counterpart Chinese Patent Application No. 202080081838.1 (3 pages in English, 2 pages in Chinese).

Chinese Office Action issued on Apr. 11, 2023, in counterpart Chinese Patent Application No. 202080081838.1 (3 pages in English, 4 pages in Chinese).

* cited by examiner

*Primary Examiner* — John S Kenyon
*Assistant Examiner* — Sara Elizabeth Bell
(74) *Attorney, Agent, or Firm* — NSIP Law

(57) ABSTRACT

The present invention relates to an antifungal composition containing a carbazole compound as an active ingredient. The carbazole compound according to the present invention inhibits the growth of not only Candida but also fungi such as yeast, and neutralizes the pathogenicity of Candida by inhibiting morphological transformation thereof. Thus, the carbazole compound is very useful as an antifungal composition capable of treating Candida infection.

6 Claims, 8 Drawing Sheets

ANTIFUNGAL COMPOSITION CONTAINING CARBAZOLE COMPOUND AS ACTIVE INGREDIENT

CROSS REFERENCE TO RELATED APPLICATIONS

This application is a U.S. National Stage Application of International Application No. PCT/KR2020/014164, filed on Oct. 16, 2020, which claims the benefit under 35 USC 119(a) and 365(b) of Korean Patent Application No. 10-2019-0132073, filed on Oct. 23, 2019 in the Korean Intellectual Property Office, the entire disclosure of which is incorporated herein by reference for all purposes.

TECHNICAL FIELD

The present invention relates to an antifungal composition containing a carbazole compound as an active ingredient.

BACKGROUND ART

Candida is one of the most common pathogens, and causes a wide range of infections, from mucosal infections in healthy people to systemic infections, which are serious infections in people with weak immunity and patients with weakened immunity. Candida lives in the oral cavity, skin, vagina, and intestinal tract of healthy humans and is controlled by the normal immune system, but causes pathogenic symptoms due to accumulation of fatigue, secretion of toxic substances due to incorrect eating habits, and decreased immunity due to diabetes, malnutrition, etc. In addition, pathogenic symptoms caused by Candida may also occur when antibiotics, corticosteroids, or immunosuppressants for disease treatment are prescribed for a long time. In particular, this pathogen is known to be an endogenous factor involved in nosocomial infections in hospitals. This pathogen acts as a serious life-threatening factor not only in patients having reduced immunity due to organ transplantation, but also in patients receiving chemotherapy, and AIDS patients. In the United States, among all hospital-acquired infections, Candida infection has continued to increase from 6% in 1980 to 10.4% in 1990, and has recently been recognized as the most common nosocomial infection. In addition, according to the recent results reported by the National Nosocomial Infections Surveillance System (NNIS) from 1992 to 1997, Candida infection ranked fourth among blood infections, and ranked second among infections of the urethra, eyes, ears, nose, and throat. To date, damage caused by Candida in hospitals worldwide is at a serious level, and is emerging as a priority to be resolved. Until now, attempts have been made to eradicate such Candida bacteria through antibiotics, but there has been difficulty in the treatment of Candida, because the treatment differs between patients and even the same antibiotics are different in terms of the scope or content of action thereof. In Korea, Candida infection accounts for about 18% of nosocomial infections, and systemic Candida infection has a mortality rate of 50% or more.

*Candida albicans* is the most representative *Candida* species for which many data are available as scientific and academic studies have been conducted from the 1950s. *Candida albicans* is a dimorphic fungus that exists as a single oval yeast cell most of the time and grows by binary fission. However, *Candida albicans* forms filamentous branching hyphae under appropriate conditions, i.e., body temperature, pH, and serum. Although the relationship between this morphological change and transformation into a pathogenic form is not yet clear, most of Candida isolated from patients in whom Candida is pathogenic form hyphae. In addition, in experiments using mice with mutant Candida that is defective in hyphal formation, Candida did not develop into candidiasis. Considering these results, it is thought that a series of correlations exist between morphological transformation and pathogenicity acquisition. Thus, many scientists have conducted a lot of research on functional analysis of genes related to the morphological change of Candida and have revealed many results.

For treatment of candidiasis, many antifungal drugs such as amphotericin B and fluconazole have been developed and used, and their efficacy has been proven. However, strong resistance to fluconazole in patients has emerged as a new problem (Infect Drug Resist. 2017; 10:237-245). Thus, there is an urgent need to develop a new drug that can avoid resistance to fluconazole.

Accordingly, the present inventors have made extensive efforts to develop an antifungal therapeutic agent that is safer and more effective than conventional agents for treating candidiasis, and as a result, have found that a compound containing carbazole exhibits an excellent antifungal effect not only against Candida but also against other fungi such as yeast and Aspergillus, thereby completing the present invention.

SUMMARY OF THE INVENTION

An object of the present invention is to provide the antifungal use of a carbazole compound having growth inhibitory and pathogenicity-neutralizing effects against not only Candida but also fungi such as yeast.

To achieve the above object, the present invention provides an antifungal composition containing, as an active ingredient, a carbazole compound selected from the group consisting of the following Formulas 1 to 8.

[Formula 1]

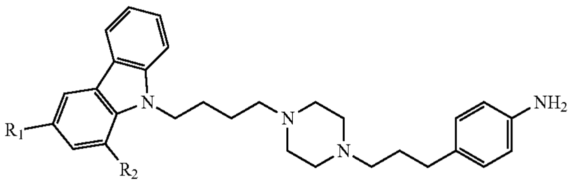

wherein $R_1$ and $R_2$ are each H or Br.

[Formula 2]

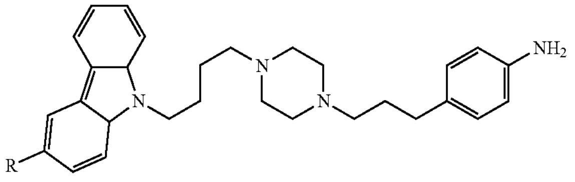

wherein R is H or $NO_2$.

[Formula 3]

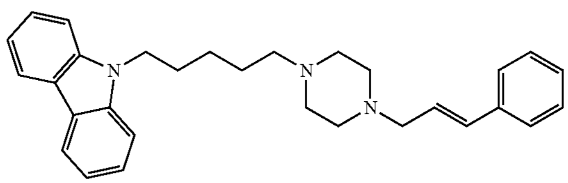

[Formula 4]

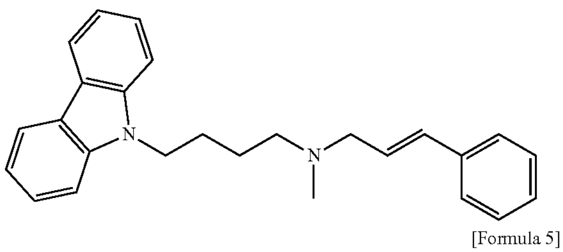

[Formula 5]

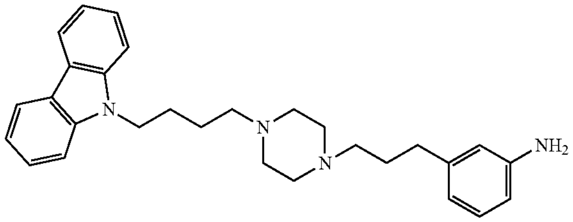

[Formula 6]

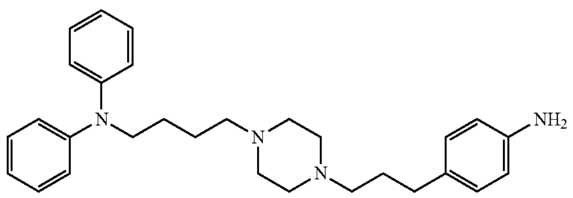

[Formula 7]

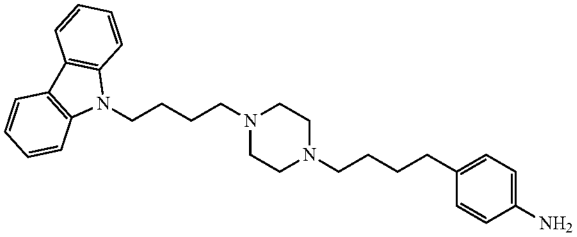

[Formula 8]

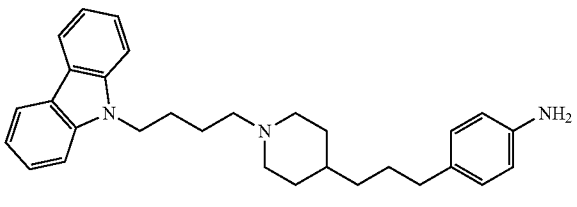

The present invention also provides the antifungal use of a carbazole compound selected from the group consisting of Formulas 1 to 8.

In the present invention, the antifungal use may be a use for inhibiting fungal infection, a use for treating fungal infection disease, or a use for killing fungal infection.

The present invention also provides the use of a carbazole compound selected from the group consisting of Formulas 1 to 8 for the manufacture of an antifungal drug.

The present invention also provides a fungus killing method comprising a step of treating a subject in need of fungus killing with a carbazole compound selected from the group consisting of Formulas 1 to 8.

The present invention also provides a method for inhibiting fungal infection comprising a step of treating a subject likely to have fungal infection with a carbazole compound selected from the group consisting of Formulas 1 to 8.

The present invention also provides a method for treating fungal infection comprising a step of administering a carbazole compound selected from the group consisting of Formulas 1 to 8 to a fungus-infected subject.

BRIEF DESCRIPTION OF DRAWINGS

FIG. 1A shows the results of testing the MICs of molecule A, B, C, D and E against *Candida albicans*, and FIG. 1B shows the results of testing the MICs of molecules F, G, H, I and J against *Candida albicans*.

DETAILED DESCRIPTION AND THE INVENTION

Figure 1A:
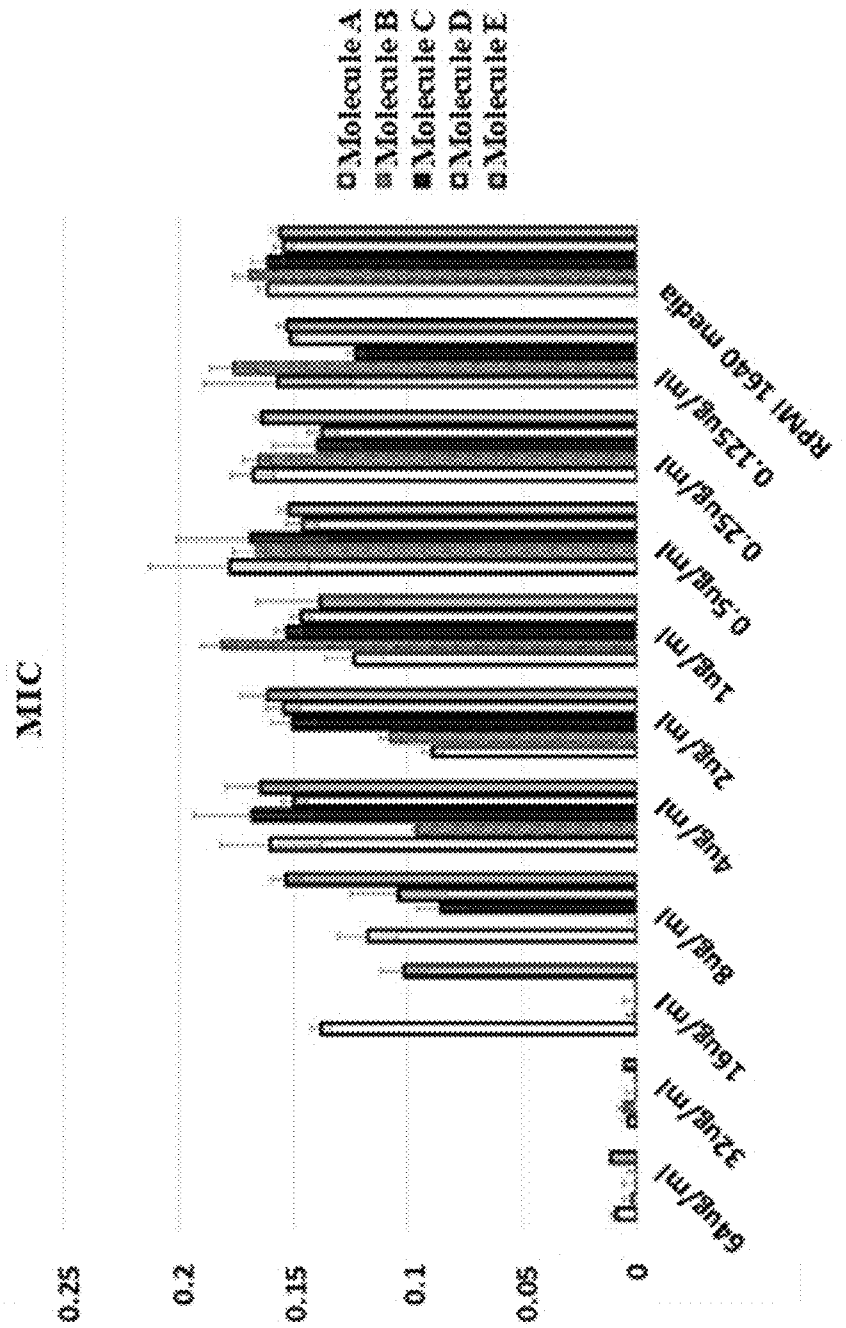
FIGS. 1A and 1B show the results of measuring the absorbance of Candida treated with carbazole compounds.

Unless otherwise defined, all technical and scientific terms used in the present specification have the same meanings as commonly understood by those skilled in the art to which the present disclosure pertains. In general, the nomenclature used in the present specification is well known and commonly used in the art.

In the present invention, it was confirmed that carbazole compounds having various structures, which are capable of acting on Candida to inhibit the growth of Candida and neutralize the pathogenicity of Candida, inhibited the growth of Candida and various fungi and exhibited a therapeutic effect in mice infected with Candida. In addition, the carbazole compound of the present invention exhibits an excellent antifungal effect in mammalian cells while being safe.

Therefore, in one aspect, the present invention is directed to an antifungal composition containing, as an active ingredient, a carbazole compound selected from the group consisting of the following Formulas 1 to 8:

[Formula 1]

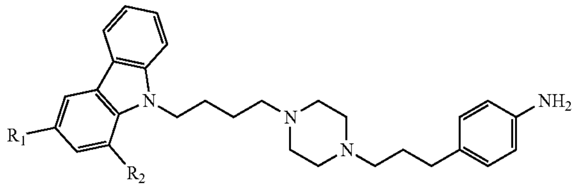

wherein $R_1$ and $R_2$ are each H or Br.

[Formula 2]

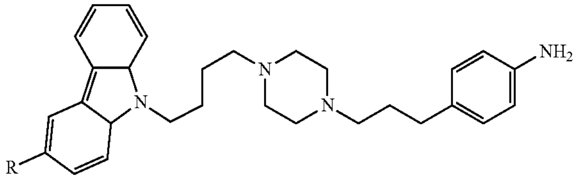

wherein R is H or $NO_2$.

[Formula 3]

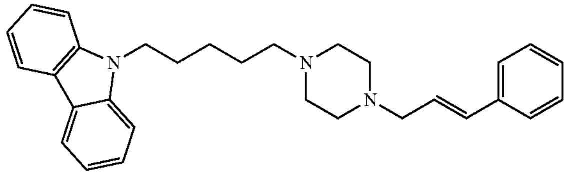

[Formula 4]

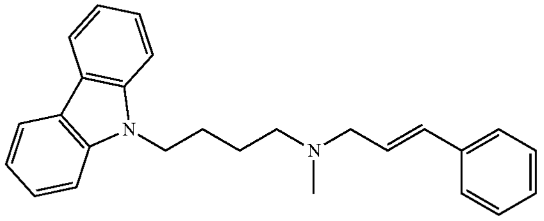

[Formula 5]

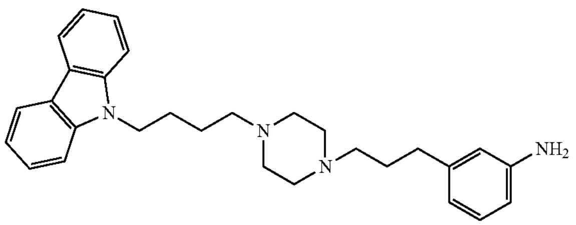

[Formula 6]

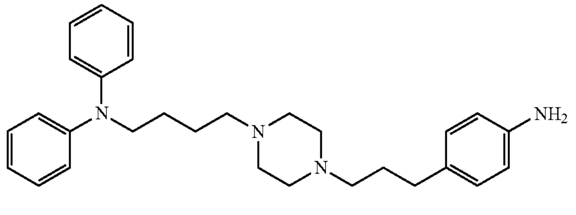

-continued

[Formula 7]

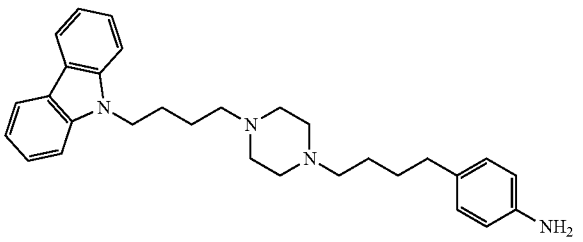

[Formula 8]

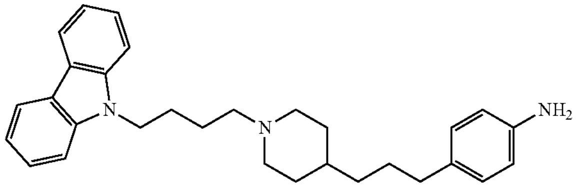

The carbazole compound of the present invention includes both a salt of the compound and an optical isomer thereof, unless otherwise specified.

When the carbazole compound is used in the form of a salt, it is preferable to select a salt suitable or acceptable for each use from among possible salts of the carbazole compound that is an active ingredient. Preferably, the salt useful in the present invention is an acid addition salt formed with a pharmaceutically acceptable free acid.

Examples of the free acid include organic acids and inorganic acids. Examples of the inorganic acid include hydrochloric acid, bromic acid, sulfuric acid, sulfurous acid, phosphoric acid, and the like, and examples of the organic acid include citric acid, acetic acid, maleic acid, fumaric acid, gluconic acid, methanesulfonic acid, acetic acid, glycolic acid, succinic acid, tartaric acid, 4-toluenesulfonic acid, galacturonic acid, embonic acid, glutamic acid, citric acid, aspartic acid, and the like, with methanesulfonic acid or hydrochloric acid being preferred.

A compound, in which $R_1$ in Formula 1 is Br and $R_2$ is H, may be expressed as molecule B in an example of the present invention. In addition, a compound, in which $R_1$ in Formula 1 is H and $R_2$ is Br, may be expressed as molecule J in an example of the present invention.

A compound, in which R in Formula 2 is H, may be expressed as molecule C in an example of the present invention. In addition, a compound, in which R in Formula 2 is $NO_2$, may be expressed as molecule G in an example of the present invention.

In addition, in an example of the present invention, Formula 3 may be expressed as molecule A, Formula 4 as molecule D, Formula 5 as molecule E, Formula 6 as molecule F, Formula 7 as molecule H, and Formula 8 as molecule I.

The compounds of Formulas 1 to 8 were produced according to the method described in Bioorganic & Medicinal Chemistry Letters 18:4670-4674, 2008.

The carbazole compound of the present invention exhibits excellent antifungal activity against Candida and various fungi. The therapeutic effect against Candida infection is due to the effect of carbazole on inhibiting the morphological transformation of Candida into a hypha which is one of pathogenic factors.

In one example of the present invention, molecule B and molecule C exhibited MICs of 8 μg/ml and 16 μg/ml, respectively, against Candida, suggesting that they have excellent antifungal activity.

In another example of the present invention, molecule B and molecule C exhibited MICs of 4 μg/ml and 4 μg/ml, respectively, against budding yeast *S. cerevisiae* and *A. fumigatus*, suggesting that they have an excellent antifungal effect. In addition, molecule B and molecule C both exhibited an MIC of 64 μg/ml against *A. fumigatus*.

The fungus in the present invention is preferably any one selected from the group consisting of *Candida* sp., *Saccharomyces* sp., *Kazachstania* sp., *Aspergillus* sp., *Cladosporium* sp., *Penicillium* sp., and combinations thereof, without being limited thereto.

As described above, the carbazole compound according to the present invention has an excellent antifungal activity against various pathogenic microorganisms, is non-toxic, and exhibits excellent effects even when used in trace amounts. Thus, the carbazole compound may be used as an additive for various antifungal agents and pharmaceutical compositions, a food preservation additive, a cosmetic additive, an additive for building materials for antifungal purposes, an additive for pesticides, and an additive for household products.

The antifungal composition of the present invention contains, as an active ingredient, the carbazole compound having antifungal activity, and thus may be used as an antifungal agent or a pharmaceutical composition for inhibiting the activity of various pathogenic microorganisms or inhibiting hyphal formation.

The antifungal composition may further contain, in addition to the carbazole compound, at least one active ingredient exhibiting the function equal or similar to the carbazole compound.

The composition of the present invention may be prepared to contain one or more pharmaceutically acceptable carriers for administration, in addition to the active ingredient described above. As the pharmaceutically acceptable carrier, one or more selected from among saline, sterile water, Ringer's solution, buffered saline, dextrose solution, maltodextrin solution, glycerol, ethanol, and mixtures thereof may be used, and if necessary, other conventional additives such as an antioxidant, a buffer, and a bacteriostatic agent may be added. In addition, a diluent, a dispersant, a surfactant, a binder and a lubricant may be additionally added to prepare injectable formulations such as an aqueous solution, suspension, emulsion, etc., pills, capsules, granules, or tablets. Furthermore, the composition of the present invention may preferably be formulated depending on each disease or component by an appropriate method known in the art or a method disclosed in Remington's Pharmaceutical Science (latest edition), Mack Publishing Company, Easton PA.

The composition according to the present invention may be administered orally or parenterally during clinical administration and may be used in the form of a general pharmaceutical formulation. For formulation, diluents or excipients may be used, such as generally used antifungal agents, fillers, extenders, binders, wetting agents, disintegrants, surfactants, etc. As the antifungal agents, at least one selected from the group consisting of ketoconazole, itraconazole, fluconazole, miconazole, clotrimazole, fenticonazole, econazole, bifonazole, oxiconazole, cloconazole, tolciclate, amphotericin B, flucytosine, griseofulvin, terbinafine, nystatin, tolnaftate, naftifine, haloprogin, ciclopirox, triclosan, norfloxacin, ciprofloxacin, and salts thereof may be used.

A solid formulation for oral administration may be prepared by mixing one or more carbazole compounds according to the present invention with at least one excipient, for example, starch, calcium carbonate, sucrose, lactose or gelatin. In addition to simple excipients, lubricants such as magnesium stearate and talc may also be used. Liquid formulations for oral administration include suspensions, solutions, emulsions or syrups, and for the liquid formulations, various excipients such as wetting agents, sweeteners, flavors, and preservatives may be used in addition to commonly used simple diluents such as water and liquid paraffin.

Formulations for parenteral administration include sterile aqueous solutions, non-aqueous solutions, suspensions, emulsions, lyophilized formulations, and suppositories.

As non-aqueous solvents or suspending agents, propylene glycol, polyethylene glycol, vegetable oils such as olive oil, injectable esters such as ethyl oleate, etc. may be used, and as the base of the suppository, Witepsol, Macrogol, Tween 61, cacao butter, laurin fat, glycerol, gelatin, etc. may be used.

The composition of the present invention may be administered parenterally (e.g., intravenously, subcutaneously, intraperitoneally or topically) or orally depending on a desired method, and the dosage thereof may vary depending on the patient's weight, age, sex, health status and diet, the time of administration, the mode of administration, excretion rate, and the severity of the disease. In addition, it is more preferable to administer the composition once to several times a day.

In addition, the carbazole compound of the present invention may be used as a food preservation additive to preserve food for a long period of time. Examples of the food include processed food products, fish meat products, tofu, jellied foods, health supplements, seasonings, bakery and confectionery, dairy products, pickled foods, fermented foods, or beverages, and the feed is limited in its applications, including livestock feed, and may be solid or liquid.

In addition, the carbazole compound having antifungal activity may be used as a cosmetic additive to prepare a cosmetic composition for keeping hands or feet clean. Examples of the cosmetic composition include soap (solid soap, liquid soap, foam soap, body soap, hand soap, etc.), cleansing foam, shampoo (hair shampoo, dry shampoo, etc.), and the like. Thereamong, soap is preferable, and in particular, the carbazole compound may be used in formulations such as liquid soap and body soap.

In addition, the carbazole compound of the present invention may be used in various applications, including additives for antifungal building materials, pesticides, household goods, etc., and may be used in combination with known antifungal agents known in the art. As an example, pesticide-related antifungal agents are described, for example, in the Pesticide Dictionary (Pesticide Manual, $12^{th}$ ed., British Crop Protection Council, 2000).

For the above-described uses, the carbazole compound of the present invention may be contained in an amount of 0.001 wt % to 99.9 wt %, preferably 0.1 wt % to 99 wt %, more preferably 1 wt % to 50 wt %, based on the total weight of the composition so as to exhibit an effect in each of the uses.

In another aspect, the present invention is directed to the antifungal use of a carbazole compound selected from the group consisting of the following Formulas 1 to 8:

[Formula 1]

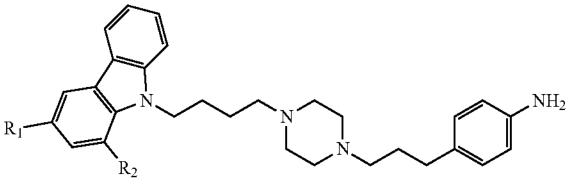

wherein $R_1$ and $R_2$ are each H or Br.

[Formula 2]

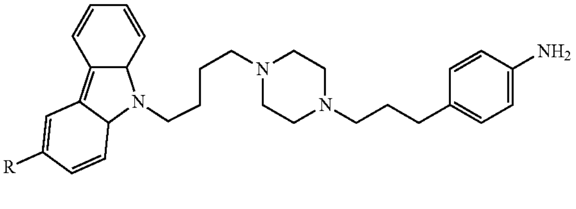

wherein R is H or $NO_2$.

[Formula 3]

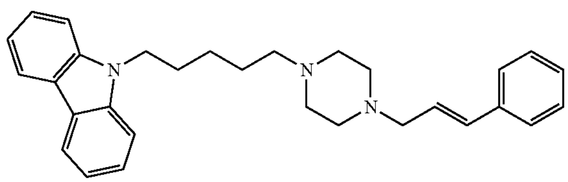

[Formula 4]

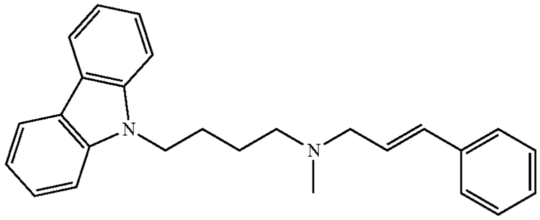

[Formula 5]

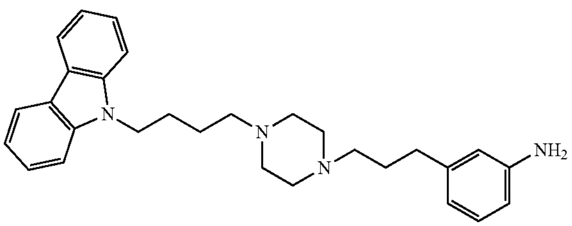

[Formula 6]

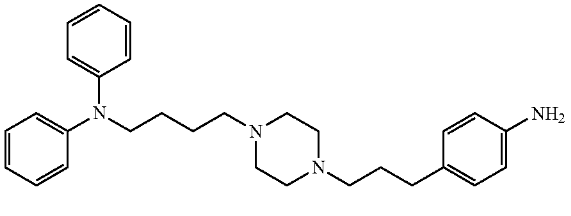

-continued

[Formula 7]

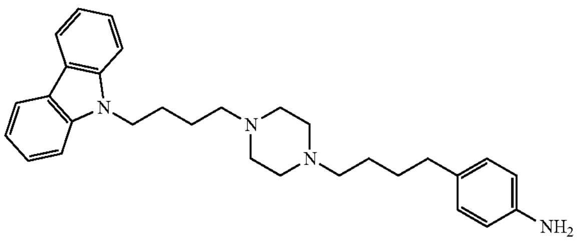

[Formula 8]

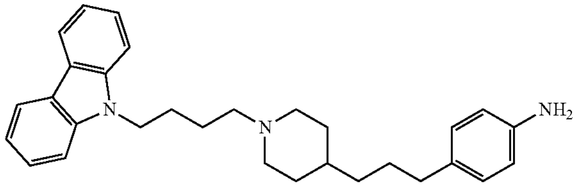

In the present invention, the antifungal use may be a use for inhibiting fungal infection, a use for treating fungal infection disease, or a use for killing fungal infection.

In another aspect, the present invention is directed to the use for the manufacture of an antifungal drug of a carbazole compound selected from the group consisting of Formulas 1 to 8.

In another aspect, the present invention is directed to a fungus killing method comprising a step of treating a subject in need of fungus killing with a carbazole compound selected from the group consisting of Formulas 1 to 8.

In another aspect, the present invention is directed to a method for inhibiting fungal infection comprising a step of treating a subject likely to have fungal infection with a carbazole compound selected from the group consisting of Formulas 1 to 8.

In another aspect, the present invention is directed to a method for treating fungal infection comprising a step of administering a carbazole compound selected from the group consisting of Formulas 1 to 8 to a fungus-infected subject.

EXAMPLES

Hereinafter, the present invention will be described in more detail with reference to examples. These examples are only for illustrating the present invention, and it will be obvious to those of ordinary skill in the art that the scope of the present invention should not be construed as being limited by these examples.

Example 1: Fungal Growth Inhibitory Effect 1-1: Inhibition of Candida Growth An inhibitory effect on Candida growth was evaluated using the CLSI M27 method, which is known as a standard method for antifungal susceptibility testing. The evaluation was performed using the broth microdilution method according to the guidelines of CLSI M27-A2. As medium, 10.4 g of RPMI-MOPS, which is RPMI-1640 medium (Gibco, Gaithersburg, MD, USA) supplemented with L-glutamine, was dissolved in 900 mL of distilled water, and then 34.53 g of 0.165 M 3-N-morpholinopropanesulfonic acid MOPS) buffer was dissolved therein to reach a final volume of 1,000 mL, followed by pH adjustment to 7.0. Then, the solution was filtered through a 0.2 μm filter, thus preparing a medium.

The carbazole compound was dissolved in triple distilled water or dimethyl sulfoxide (DMSO) (Sigma) to a concentration of 20 mg/mL. This antifungal agent was diluted serially from a concentration of 64 μg/mL to a final concentration between 0.125 μg/mL.

A Candida strain was incubated in yeast extract peptone dextrose (YPED) for 16 hours at 30° C., and adjusted to 1.0 turbidity (measured by a spectrophotometer at 600 nm) so that the fungal concentration was about $2.0\times10^7$ CFU/mL. The fungal solution was washed with triple distilled water, and then diluted again with RPMI-MOPS medium, and 100 μL of the fungal solution was dispensed into each of well Nos. 1 to 10 of a 96-well microplate (final cell concentration: $2.0\times10^4$ CFU/mL). In addition, 100 μL of the fungal solution was dispensed into well No. 11 (a growth control well), and only 100 μL of RPMI-MOPS medium was dispensed into well No. 12 (a medium control well). After completion of fungal inoculation, the microplate was incubated at 37° C. for 24 hours.

For evaluation of the results, data were obtained by measuring the absorbance using a microplate spectrophotometer to prevent errors by the inspector. Table 1 shows the absorbance of the Candida strain treated with the carbazole-containing compound.

TABLE 1

| | 64 μg/ml | 32 μg/ml | 16 μg/ml | 8 μg/ml | 4 μg/ml | 2 μg/ml | 1 μg/ml | 0.5 μg/ml | 0.25 μg/ml | 0.125 μg/ml | 0 μg/ml | RPMI media |
|---|---|---|---|---|---|---|---|---|---|---|---|---|
| Molecule | 0.043 | 0.047 | 0.042 | 0.041 | 0.137 | 0.143 | 0.224 | 0.198 | 0.199 | 0.209 | 0.216 | 0.039 |
| B | 0.044 | 0.045 | 0.042 | 0.041 | 0.132 | 0.143 | 0.228 | 0.199 | 0.201 | 0.229 | 0.209 | 0.038 |
| | 0.036 | 0.04 | 0.036 | 0.034 | 0.135 | 0.152 | 0.208 | 0.218 | 0.212 | 0.206 | 0.197 | 0.038 |
| Molecule | 0.04 | 0.039 | 0.04 | 0.136 | 0.24 | 0.198 | 0.193 | 0.25 | 0.193 | 0.156 | 0.207 | 0.036 |
| C | 0.039 | 0.039 | 0.038 | 0.124 | 0.195 | 0.188 | 0.194 | 0.199 | 0.162 | 0.17 | 0.206 | 0.049 |
| | 0.044 | 0.043 | 0.044 | 0.122 | 0.194 | 0.19 | 0.196 | 0.182 | 0.189 | 0.168 | 0.195 | 0.04 |

In the data, the concentration at which growth was inhibited based on the medium control well was determined as MIC (minimum inhibitory concentration), and the results are shown in Table 2 below and FIG. 1.

TABLE 2

| Molecule | MIC |
|---|---|
| Molecule A | 32 ug/ml |
| Molecule B | 8 ug/ml |
| Molecule C | 16 ug/ml |
| Molecule D | 16 ug/ml |
| Molecule E | 32 ug/ml |
| Molecule F | 32 ug/ml |
| Molecule G | 16 ug/ml |
| Molecule H | 32 ug/ml |
| Molecule I | 32 ug/ml |
| Molecule J | 32 ug/ml |

Figure 1B:
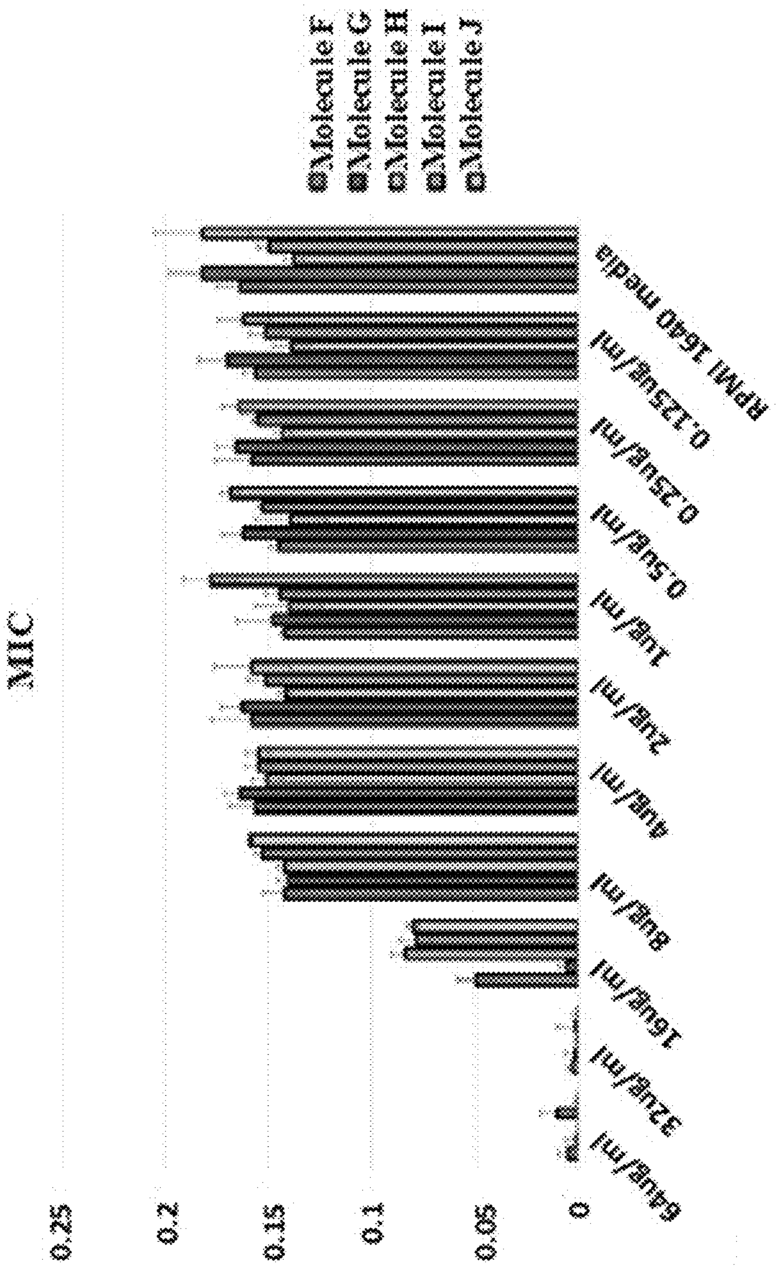

As a result, molecule B and molecule C exhibited MICs of 8 μg/ml and 16 μg/ml, respectively, against Candida (FIG. 1). That is, it could be seen that these molecules had a growth inhibitory effect against Candida.

1-2; Inhibition of Growth of *S. cerevisiae* and *A. fumigatus*

In the same manner as in Example 1-1, a MIC test was performed for budding yeast (*S. cerevisiae*) and *A. fumigatus*.

Figure 2:
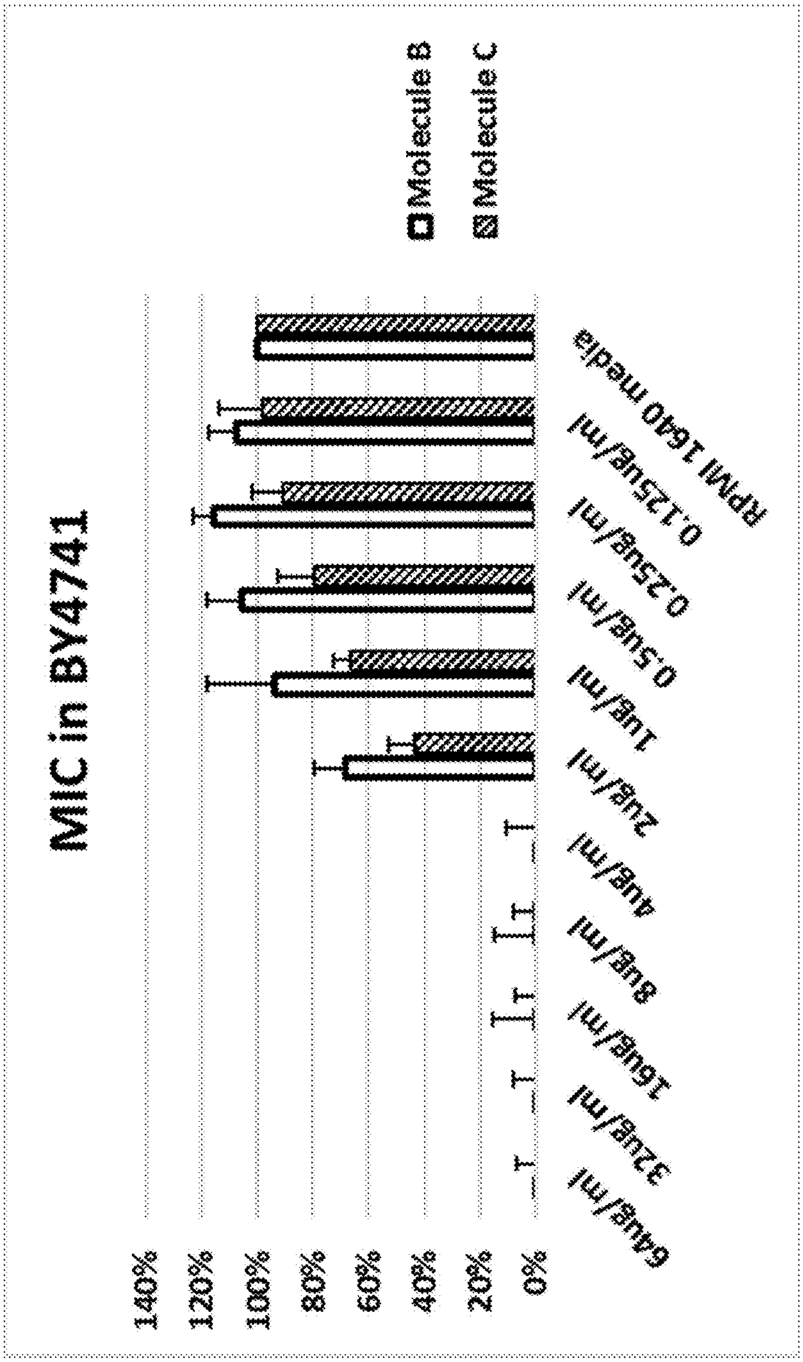
FIG. 2 shows the results of measuring the MICs of carbazole compounds B and C against *S. cerevisiae*.
Figure 3:
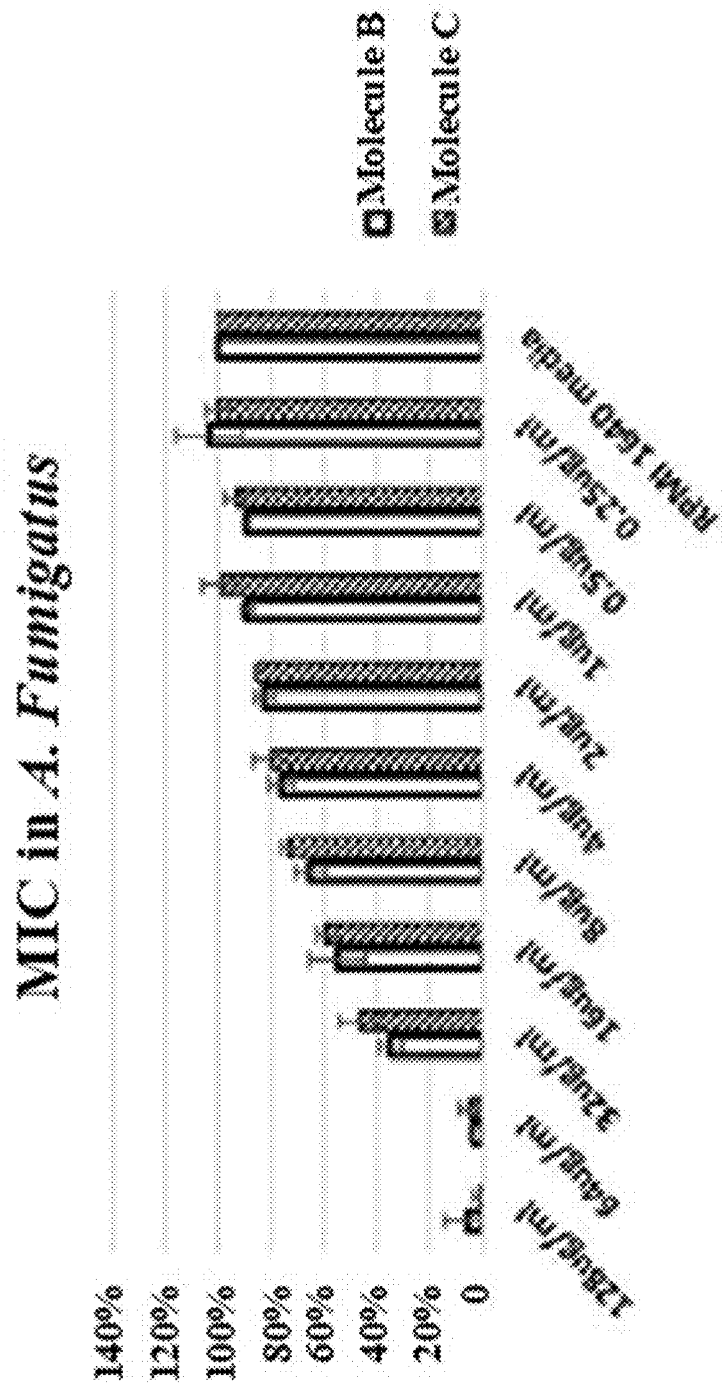
FIG. 3 shows the results of measuring the MICs of carbazole compounds B and C against *A. fumigatus*.

As a result, the MICs of molecule B and molecule C against the yeast were all 4 μg/ml, which was lower than the MICs against Candida (FIG. 2). In addition, in measurement of the MICs against *A. fumigatus* that causes aspergillosis, it could be seen that molecule B and molecule C inhibited the growth of *A. fumigatus* at the same concentration of 64 μg/ml (FIG. 3).

Therefore, it could be confirmed that the two compounds were effective not only against Candida but also against other fungi.

Example 2: Cytotoxicity Evaluation

The cytotoxicity of the carbazole compound to mammalian cells was evaluated using the human cervical cancer cell line HeLa.

Cells were seeded into a 96-well microplate at a density of $1.0\times10^4$ cells per well, and cultured in 10% FBS-containing DMEM for 24 hours at 37° C. Then, the medium was removed, each well was washed once with PBS and then treated with the synthesized compound diluted in DMEM serially from a concentration of 64 μg/ml to a concentration of 1 μg/ml. 16 hours after treatment with the compound, cytotoxicity was measured using MTS.

Figure 4:
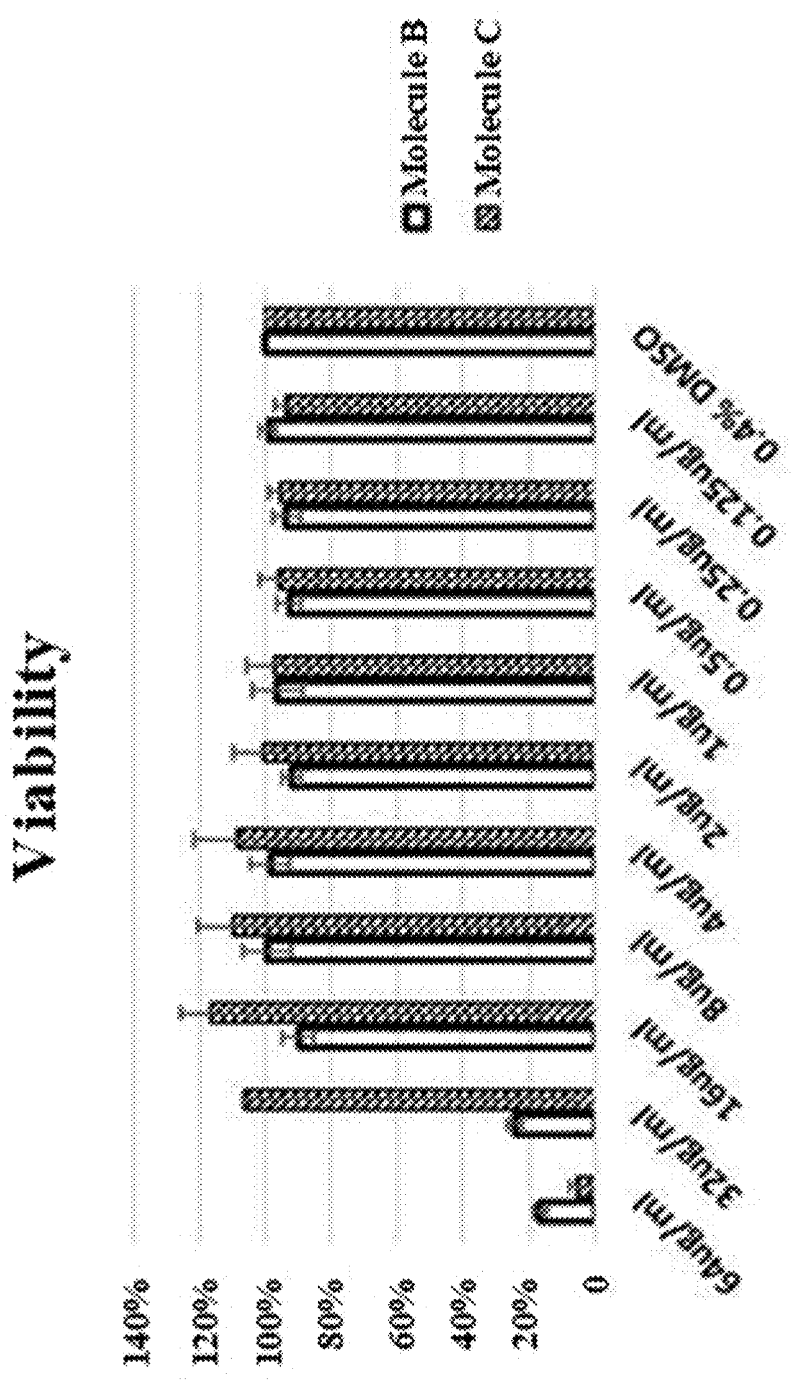
FIG. 4 shows the results of evaluating the cytotoxicity of carbazole compounds B and C to mammalian cells (HeLa cells).

As a result, it was confirmed that molecule C did not show toxicity to the mammalian cells up to a concentration of 32 μg/ml, and molecule B did not show toxicity to the mammalian cells up to a concentration of 16 μg/ml (FIG. 4). In addition, it can be seen that this concentration has the effect of inhibiting the growth of Candida and does not show toxicity to mammalian cells. Thus, it was confirmed that the compound of the present invention is harmless to mammalian cells and can inhibit the growth of Candida.

Example 3: Measurement of Survival Rate of Candidiasis Mouse Models

For Candida infection, SC5314, a wild-type strain, was used, and 6-week-old Balb/C female mice were used. The mice were divided into two groups, each consisting of 5 mice, and the survival rate thereof was monitored.

3-1: Mice Infected with Candida by Tail Vein Injection $5.0\times10^5$ Candida cells were diluted in 200 μl of PBS and mice were infected with the dilution by tail vein injection. From day 1 after infection, the control group was inoculated with 200 μl of PBS by tail vein injection, the experimental groups were weighed and treated with molecule B (diluted in 100 μl of PBS) in an amount of 8 mg/kg by tail vein injection or treated with molecule C (diluted in 100 μl of PBS) in an amount of 16 mg/kg by tail vein injection.

Figure 5:
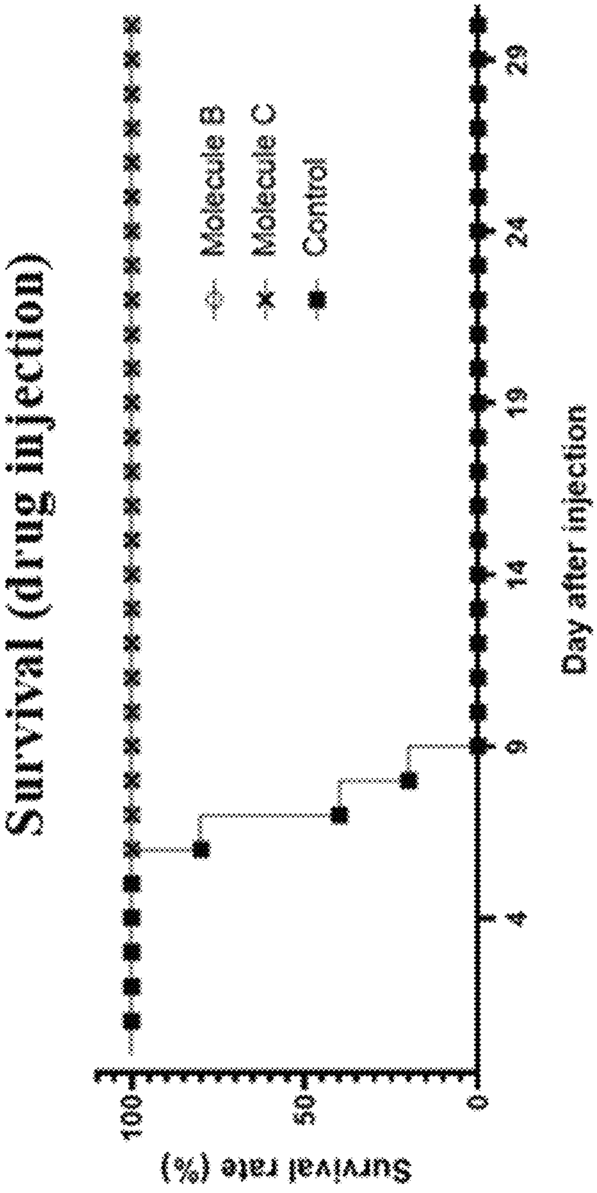
FIG. 5 shows the results of measuring the survival rate of candidiasis mouse models treated with carbazole compounds B and C by tail vein injection.

As a result, the group not injected with the carbazole compound showed a survival rate of 0% on day 9, and the other mice injected with the two compounds survived for more than 30 days (FIG. 5).

3-2: Mice Infected with Candida Through Drinking Water

The control group of the experiment using drinking water was provided with normal drinking water daily after Candida infection performed by tail vein injection as described in Example 3-1, and the experimental groups were provided daily with drinking water treated with molecule B at a concentration of 16 μg/ml or with drinking water treated with molecule C at a concentration of 32 μg/ml. The survival rates of the mice were monitored daily for 2 weeks.

Figure 6:
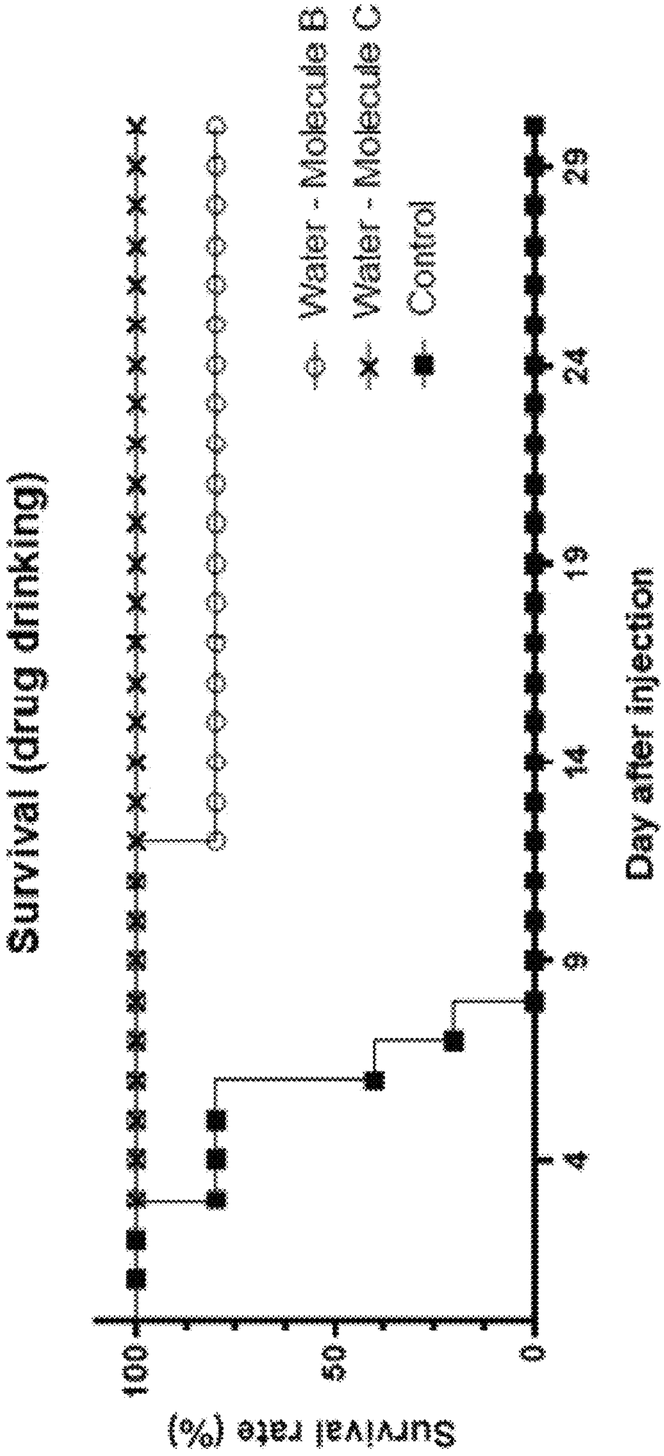
FIG. 6 shows the results of measuring the survival rate of candidiasis mouse models treated with carbazole compounds B and C diluted in drinking water.

As a result, the Candida-infected mice that drank normal drinking water showed a survival rate of 0% within 9 days, but the mice that drank the drinking water treated with molecule B or molecule C showed a survival rate of 100% and 80%, respectively (FIG. 6). That is, it could be seen that the compound of the present invention had an effect on the treatment of Candida infection.

3-3: Evaluation of Extent of Kidney Infection in Candida-Infected Mice

After Candida infection performed by tail vein injection as described in Example 3-1, the mice showing the following conditions based on humane euthanasia standards were euthanized using $CO_2$, and the kidneys were collected therefrom and the extents of infection thereof were compared: inability to eat food or drink water; abnormal breathing; dull and stiff hair; reduced movement; or bent posture or body tremor.

Figure 7:
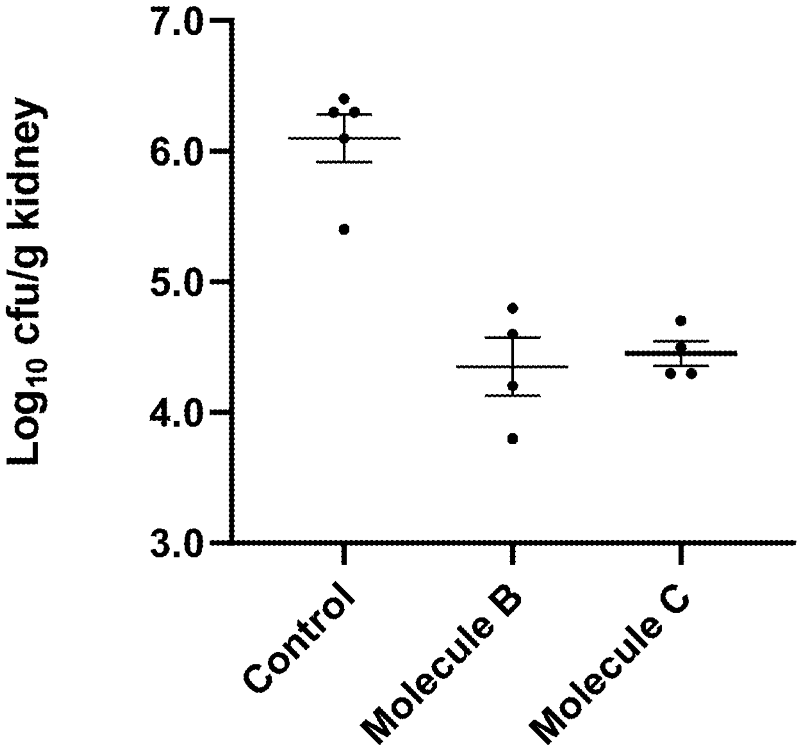
FIG. 7 shows the results of evaluating the extent of Candida infection in the kidneys of candidiasis mouse models treated with carbazole compounds B and C by tail vein injection.

As a result of examining the extent of infection after collecting the kidneys from the control mice and the mice of the two experimental groups, the mice of the groups treated with molecule B and molecule C, respectively, showed a very low extent of kidney infection compared to the infection of the kidneys of the control mice (FIG. 7). That is, it can be seen that the carbazole compound of the present invention exhibits a significant effect on the treatment of Candida infection.

Although the present invention has been described in detail with reference to specific features, it will be apparent to those skilled in the art that this description is only of a preferred embodiment thereof, and does not limit the scope of the present invention. Thus, the substantial scope of the present invention will be defined by the appended claims and equivalents thereto.

INDUSTRIAL APPLICABILITY

The carbazole compound according to the present invention inhibits the growth of not only Candida but also fungi such as yeast, and neutralizes the pathogenicity of Candida by inhibiting morphological transformation thereof. Thus, the carbazole compound is very useful as an antifungal composition capable of treating Candida infection.

The invention claimed is:

1. A method of killing fungus comprising treating a subject in need of killing the fungus with a carbazole compound selected from the group consisting of Formulas 1, 2, and 4-8:

[Formula 1]

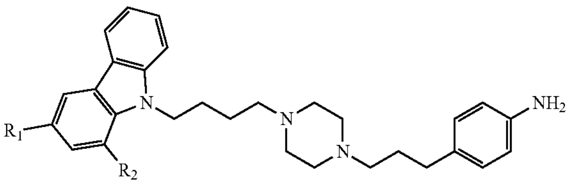

wherein $R_1$ is Br and $R_2$ is H;

[Formula 2]

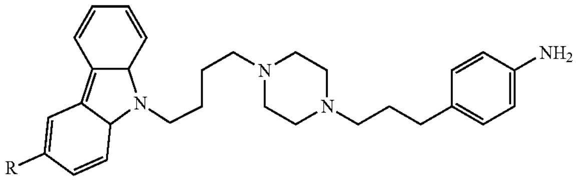

wherein R is H or $NO_2$;

[Formula 4]

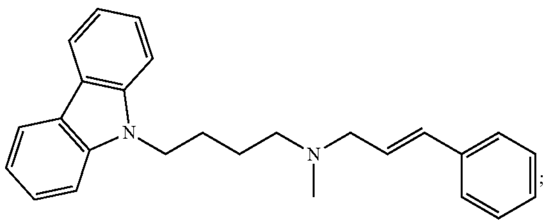

[Formula 5]

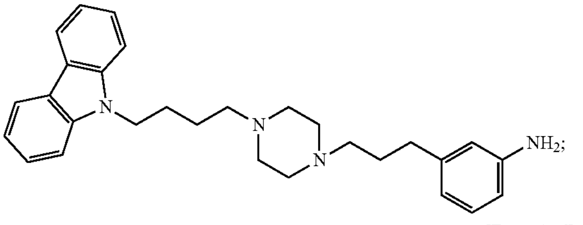

[Formula 6]

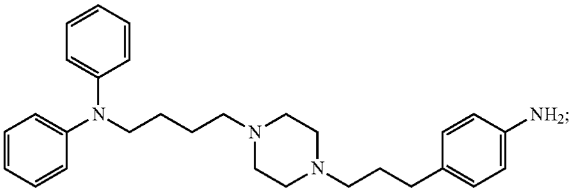

[Formula 7]

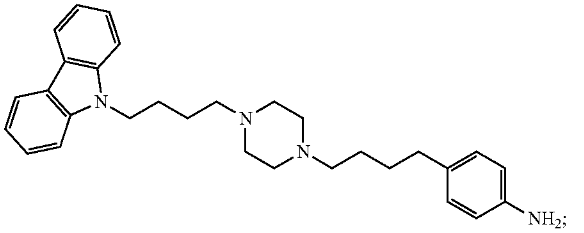

and

[Formula 8]

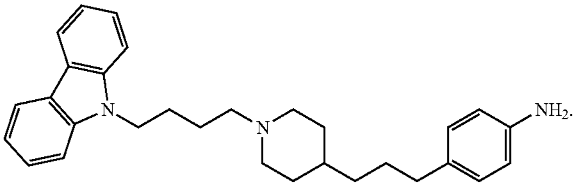

2. The method of claim 1, wherein the fungus is any one selected from the group consisting of *Candida* sp., *Saccha-* romyces sp., *Kazachstania* sp., *Aspergillus* sp., *Cladosporium* sp., *Penicillium* sp. and combinations thereof.

3. A method of inhibiting fungal infection comprising treating a fungus-infected subject with a carbazole compound selected from the group consisting of Formulas 1, 2, and 4-8:

[Formula 1]

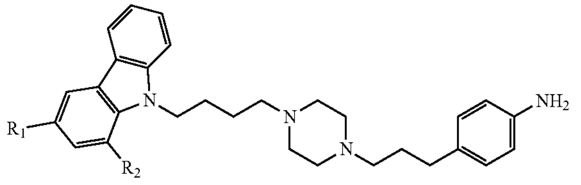

wherein $R_1$ is Br and $R_2$ is H;

[Formula 2]

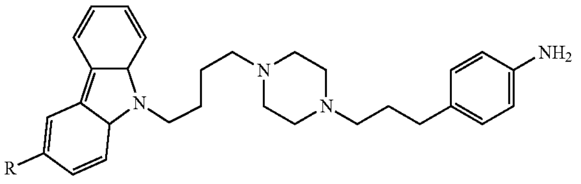

wherein R is H or $NO_2$;

[Formula 4]

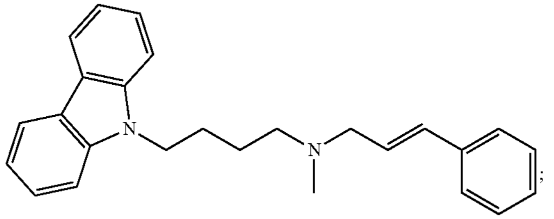

[Formula 5]

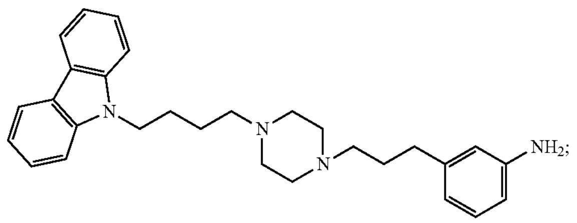

[Formula 6]

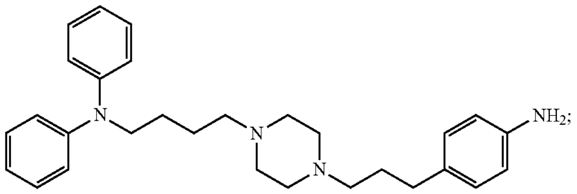

-continued

[Formula 7]

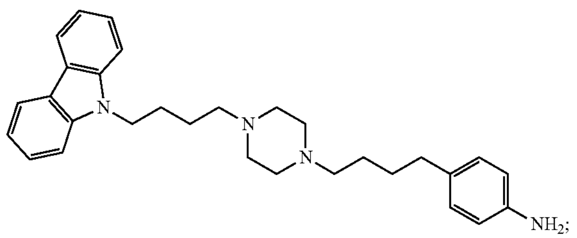

and

[Formula 8]

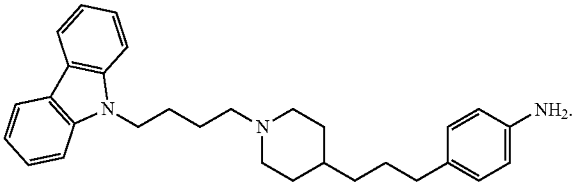

4. The method of claim 3, wherein the fungus is any one selected from the group consisting of *Candida* sp., *Saccharomyces* sp., *Kazachstania* sp., *Aspergillus* sp., *Cladosporium* sp., *Penicillium* sp. and combinations thereof.

5. A method of treating fungal infection comprising administering an antifungal composition comprising a carbazole compound selected from the group consisting of Formulas 1, 2, and 4-8, to a fungus-infected subject:

[Formula 1]

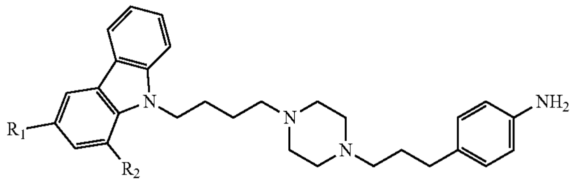

wherein $R_1$ is Br and $R_2$ is H;

[Formula 2]

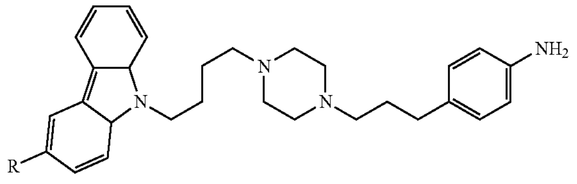

wherein R is H or $NO_2$;

[Formula 4]
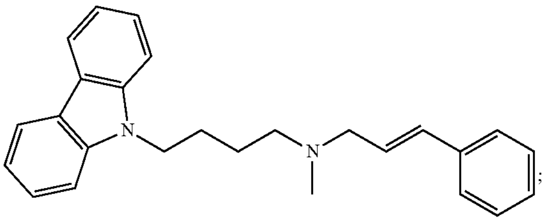
;
[Formula 5]
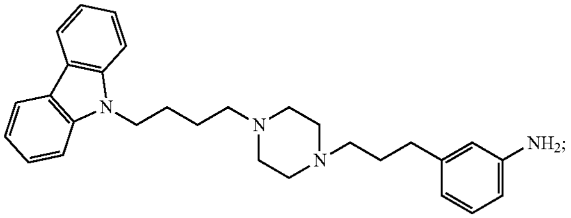
[Formula 6]
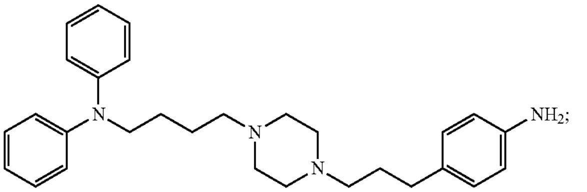
-continued
[Formula 7]
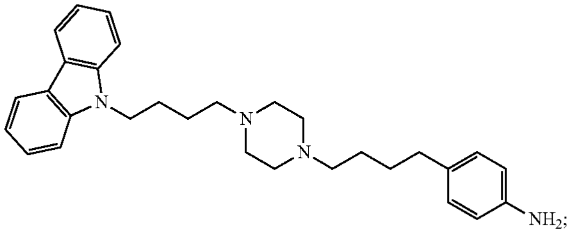
and
[Formula 8]
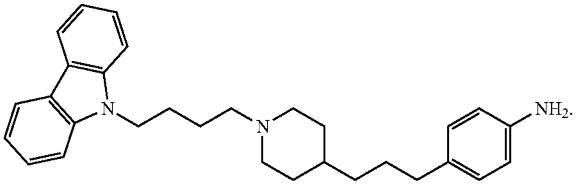
6. The method of claim 5, wherein the fungus is any one selected from the group consisting of *Candida* sp., *Saccharomyces* sp., *Kazachstania* sp., *Aspergillus* sp., *Cladosporium* sp., *Penicillium* sp. and combinations thereof.
* * * * *